(12) United States Patent
Mahnashi et al.

(10) Patent No.: US 8,866,542 B1
(45) Date of Patent: Oct. 21, 2014

(54) LOW FREQUENCY FILTER FOR BIOMEDICAL APPLICATIONS

(71) Applicants: King Fahd University of Petroleum and Minerals, Dhahran (SA); King Abdulaziz City for Science and Technology, Riyadh (SA)

(72) Inventors: Yaqub Al-Hussain Mahnashi, Dhahran (SA); Hussain Abdullah Alzaher, Dhahran (SA)

(73) Assignees: King Fahd University of Petroleum and Minerals, Dhahran (SA); King Abdulaziz City for Science and Technology, Riyadh (SA)

( * ) Notice: Subject to any disclaimer, the term of this patent is extended or adjusted under 35 U.S.C. 154(b) by 0 days.

(21) Appl. No.: 13/926,942

(22) Filed: Jun. 25, 2013

(51) Int. Cl.
*H03K 5/00* (2006.01)
*A61B 5/00* (2006.01)
*H03H 11/12* (2006.01)

(52) U.S. Cl.
CPC .......... *A61B 5/7203* (2013.01); *H03H 11/1252* (2013.01)
USPC .......................................... 327/558; 327/552

(58) Field of Classification Search
USPC ........................... 327/552, 558, 554, 148, 157
See application file for complete search history.

(56) References Cited

U.S. PATENT DOCUMENTS

| | | | |
|---|---|---|---|
| 5,175,510 A | 12/1992 | Satomäki | |
| 7,023,263 B2 * | 4/2006 | Chang et al. | 327/558 |
| 7,466,192 B2 * | 12/2008 | Nakabo et al. | 327/558 |
| 8,368,461 B2 * | 2/2013 | Blanc | 327/558 |

OTHER PUBLICATIONS

Yaqub Mahnashi and Hussain Alzahar, "Applying the Difference Term Approach for Low Frequency Biomedical Filter," Published on Jun. 30, 2012.

* cited by examiner

*Primary Examiner* — Hai L Nguyen
(74) *Attorney, Agent, or Firm* — Richard C Litman

(57) ABSTRACT

The low frequency filter for biomedical applications scales down the pole frequency while accomplishing a 5-bit reduction in the cut off frequency. This is made possible through adding a passive resistor in the forward path of the op-amp-based integrator, introducing a difference term of the pole frequency. Moreover, the filter topology is modified to avoid changing the quality factor. An exemplary second-order low pass filter is designed and simulated. Simulation results show that the pole frequency is scaled down from 1.43 MHz to 4.97 kHz, while maintaining tuning of 30% around the nominal value by controlling only one resistor.

2 Claims, 4 Drawing Sheets

LOW FREQUENCY FILTER FOR BIOMEDICAL APPLICATIONS

BACKGROUND OF THE INVENTION

1. Field of the Invention

The present invention relates to active filters, and particularly to a low frequency filter for biomedical applications.

2. Description of the Related Art

Very low frequency filters have a wide range of applications in biomedical signal processing. The bandwidth of an Electroencephalogram (EEG), for example, refers to the monitored signal due to the brain activities, and of an Electrocardiogram (ECG), which is a test for the electrical activities that are being recorded due to heart beats, are 0.1-30 Hz and 0.01-100 Hz, respectively. Amplification and pre-filtering of these signals are mandatory before further digital signal processing (DSP). However, such very low frequency filters need large passive components values, which cannot be implemented in standard analog integrated circuit (IC) fabrication. Typical values for integrated resistors are from several ohms to 40 k$\Omega$, and for capacitors are from 0.5 pF to 50 pF. This has been a challenging design problem due to the difficulty in developing efficient methods to achieve large time constants using integrated passive elements.

Thus, a low frequency filter for biomedical applications solving the aforementioned problems is desired.

SUMMARY OF THE INVENTION

The low frequency filter for biomedical applications uses a novel approach to scale down the pole frequency while accomplishing a 5-bit reduction in the cut off frequency. This is made possible through adding a passive resistor in the forward path of the op-amp-based integrator, introducing a difference term of the pole frequency. Moreover, the filter topology is modified to avoid changing the quality factor. An exemplary second-order low pass filter is designed and simulated. Simulation results show that the pole frequency is scaled down from 1.43 MHz to 4.97 kHz, while maintaining tuning of 30% around the nominal value by controlling only one resistor.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
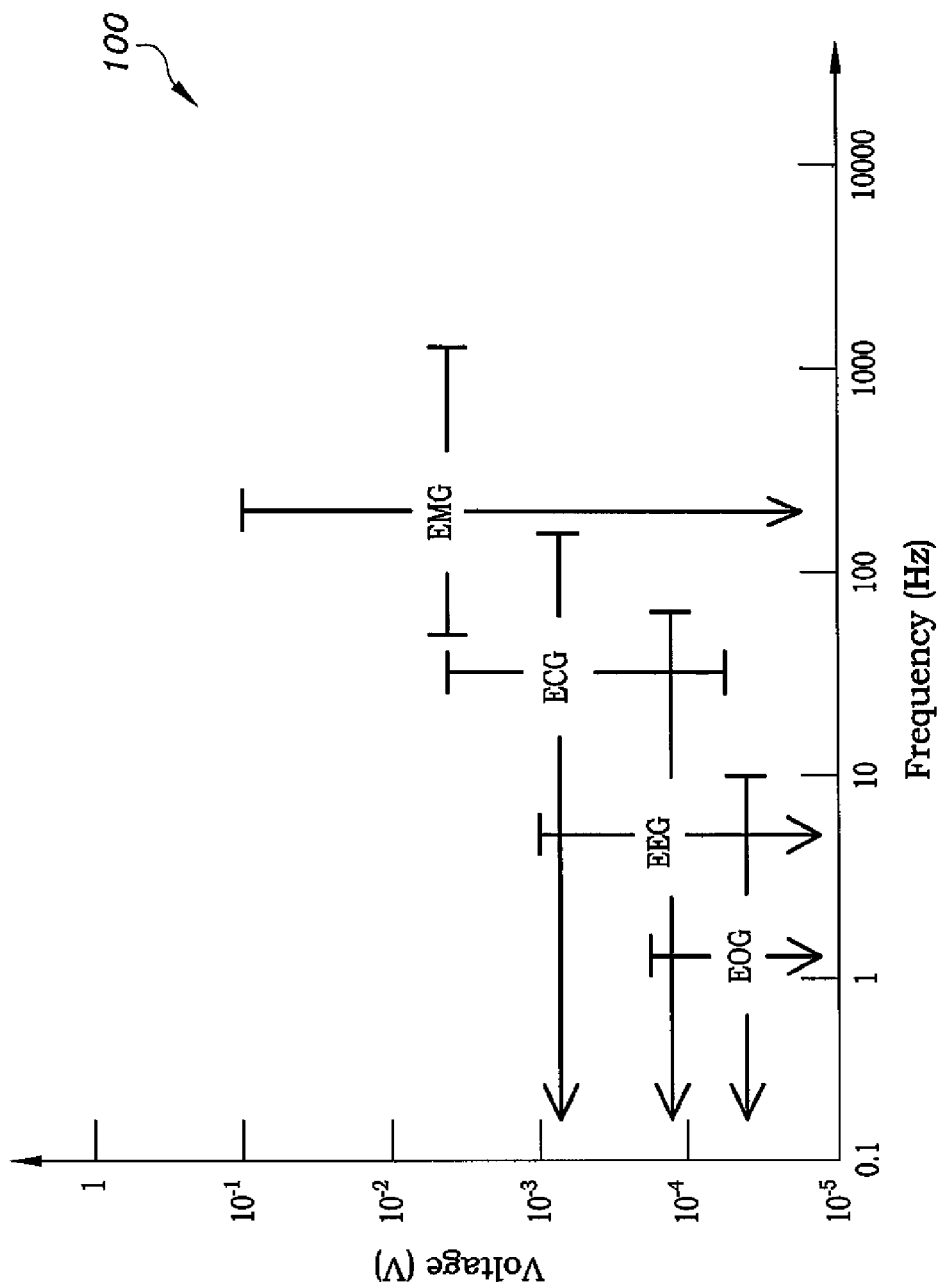
FIG. 1 is a plot of voltage and frequency ranges of some representative signals produced by biomedical testing devices, e.g., EEG, ECG, etc.
Figure 2:
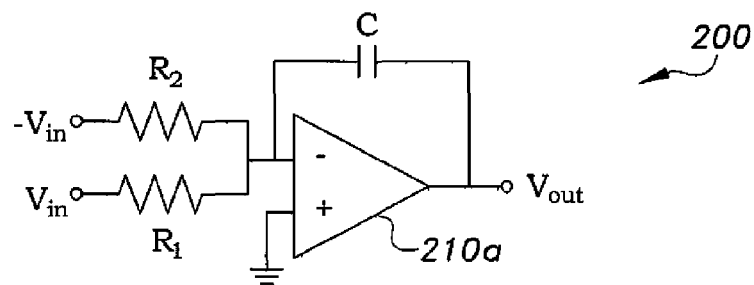
FIG. 2 is a schematic diagram of an integrator used in the low frequency filter for biomedical applications according to the present invention.

The low frequency filter for biomedical applications uses a novel approach to scale down the pole frequency while accomplishing a 5-bit reduction in the cut off frequency. The amplitude and frequency ranges of some physiological signals are shown in plot 100 of FIG. 1. The present filter is designed to address these low frequency bio signals. As shown in FIG. 2, this is made possible through adding a passive resistor in the forward path at the input of op-amp 210a of integrator 200, introducing a difference term of the pole frequency. Moreover, the filter topology is modified to avoid changing the quality factor. An exemplary second-order low pass filter is designed and simulated. Simulation results show that the pole frequency is scaled down from 1.43 MHz to 4.97 kHz, while maintaining tuning of 30% around the nominal value by controlling only one resistor.

The present low frequency filter for biomedical applications 300 (shown in FIG. 3) employs a new CMOS circuit technique for implementing a very low frequency Active-RC-based filter by applying a difference term approach that realizes a very low frequency oscillator. The filter 300 employs three op amps, 210a, 210b and 210c. The transfer function of the low pass filter is given in the following equation:

$$\frac{V_{LP}}{V_{in}} = \frac{K}{S^2 + \left(\frac{Q}{BW}\right)S + \omega^2}, \quad (1)$$

where K is the gain of the filter, Q is the quality factor, BW represents the bandwidth and $\omega$ is the corner frequency (3-dB frequency). The corner frequency of the low pass filter is given by:

$$f = \left(\frac{1}{2\pi CR}\right). \quad (2)$$

To get low frequencies in the range of a few hertz to few kilo-hertz, large capacitors and resistors are needed. One novel approach to scale down the frequency is to introduce a difference term of $R_1$ and $R_2$, m=$R_1$-$R_2$, in the $\omega$ term. So, as m decreases, the frequency is scaled down and a very low corner frequency can be obtained. The challenge in this approach in filter design is to introduce the difference term m, not only in the pole frequency $\omega$, but also in the s-coefficient term, (Q/BW) to cancel the effect of m in Q, and hence the quality factor can be controlled via the ratio of resistors $R_x/R_y$, independent of $R_1$-$R_2$. The filter topology is adjusted to resolve this problem by introducing a square of the difference term $m^2$, in the pole frequency and m in the s-coefficient term, and hence the effect of m on the Q is cancelled. Also $m^2$ is introduced in the numerator coefficient such that the gain is not disturbed.

Figure 3:
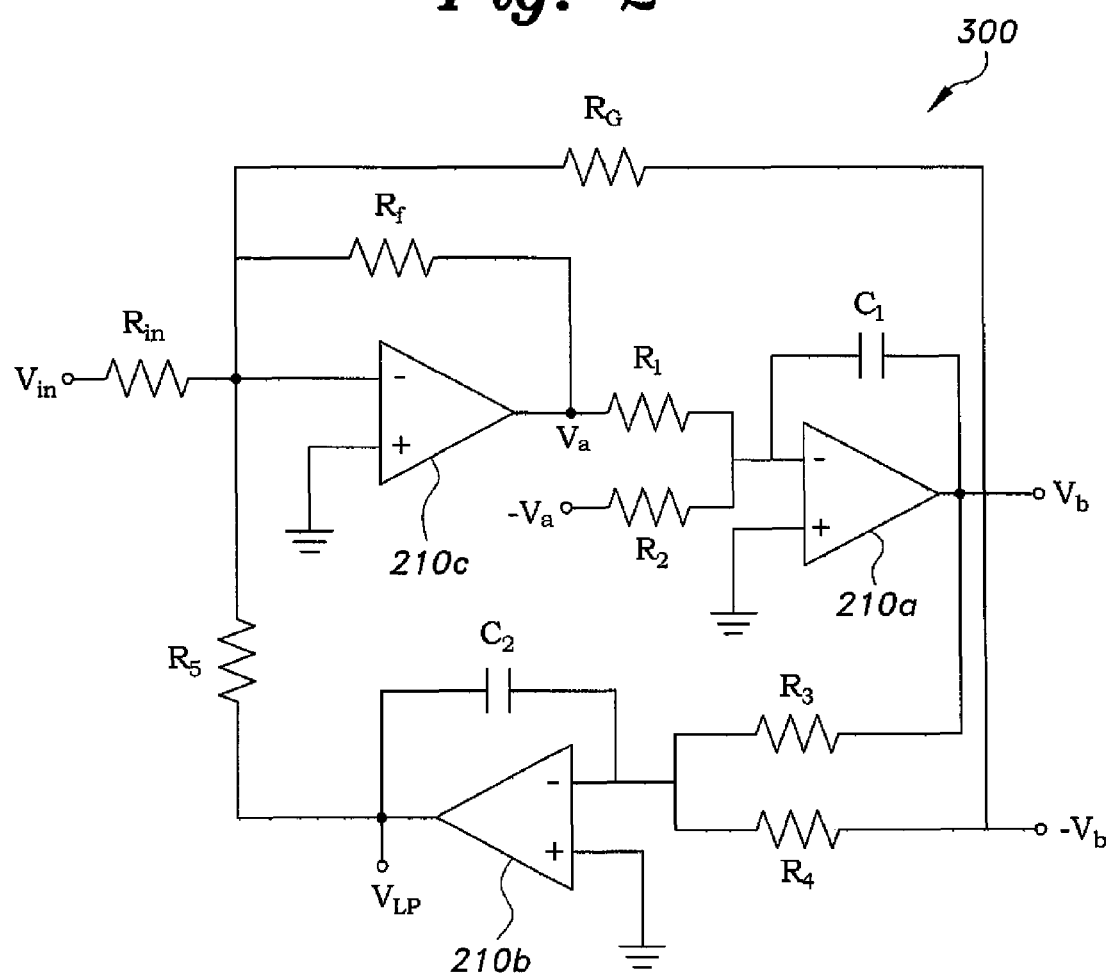
FIG. 3 is a schematic diagram of the low frequency filter for biomedical applications according to the present invention.

A low pass filter can be obtained using the integrator shown in FIG. 2 in a two-integrator loop topology. The transfer function of the present low frequency filter for biomedical application, shown in FIG. 3 is obtained as follows:

$$\frac{V_{LP}}{V_{in}} = \frac{\frac{R_f(R_1 - R_2)(R_3 - R_4)}{C_1 C_2 R_1 R_2 R_3 R_4 R_{in}}}{S^2 + S\left(\frac{R_f(R_1 - R_2)}{C_2 R_1 R_2 R_G}\right) + \frac{R_f(R_1 - R_2)(R_3 - R_4)}{C_1 C_2 R_1 R_2 R_3 R_4 R_5}}. \quad (3)$$

From the above transfer function, and assuming $R_f$=$R_5$=R, $R_1$=$R_3$, $R_2$=$R_4$, and $C_1$=$C_2$=C, we can obtain the DC gain, the corner frequency and the quality factor as follows:

$$DCGain = \frac{R}{R_{in}}, Q = \frac{R_G}{R}, 2\pi f = \left(\frac{(R_1 - R_2)}{CR_1R_2}\right). \quad (4)$$

In this topology, the DC gain, the quality factor, and the corner frequency can be controlled independently (Eqn. 4). Moreover, the corner frequency can be scaled down by exploiting the presence of the difference term of the resistors in the numerator. However, this technique suffers from high sensitivity (Equation 6). The sensitivity for the present filter 300 is given below:

$$S_{R_1}^Q = S_{R_2}^Q = S_\omega^Q = 0, S_{R_g}^Q = -S_R^Q = S_{DCGain}^Q = 1, \quad (5)$$

$$S_{R_1}^\omega = \frac{R_2}{R_1 - R_2}. \quad (6)$$

Figure 4:
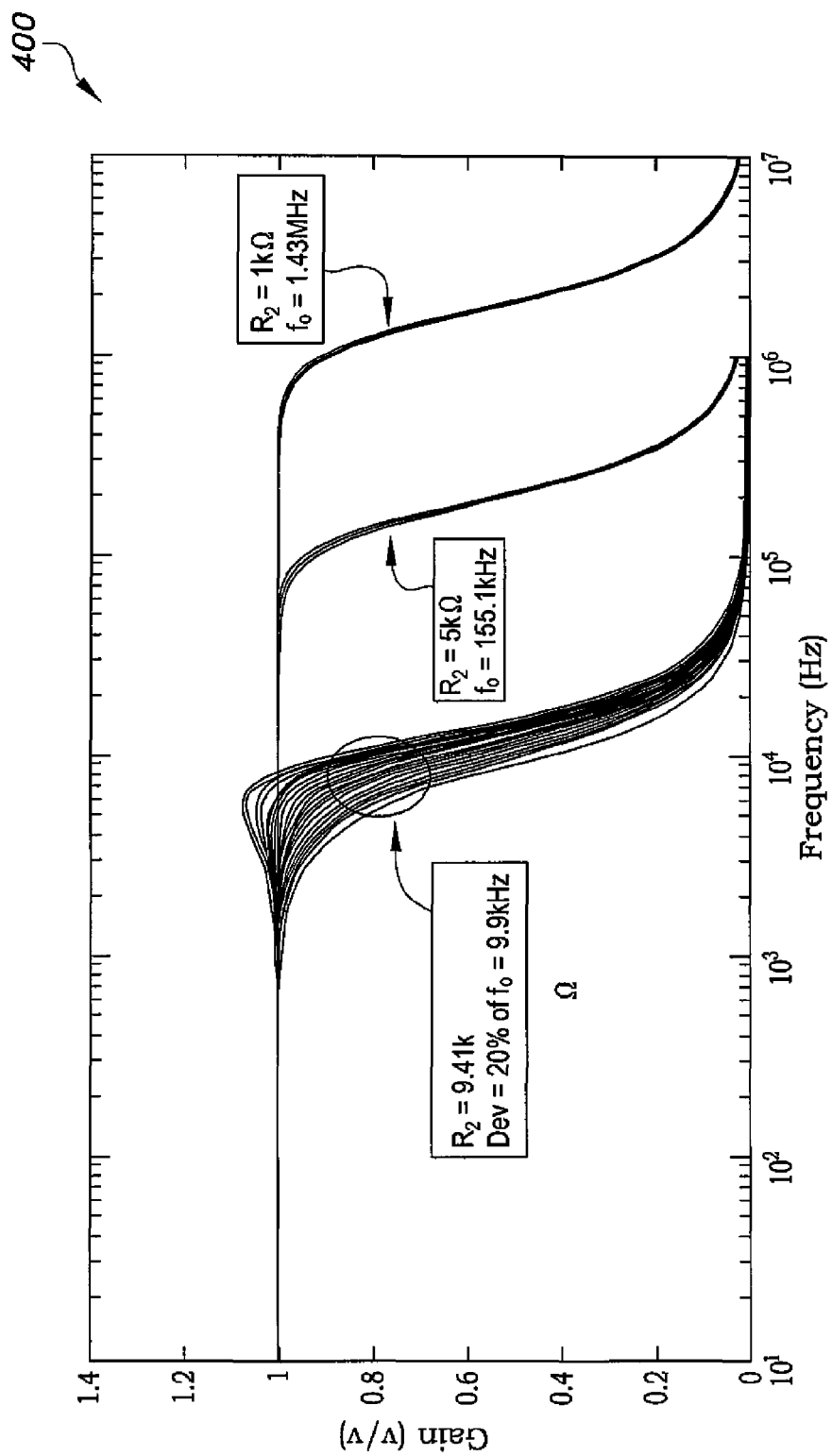
FIG. 4 is a plot of the frequency response of the low frequency filter of FIG. 3, comparing the response when $R_2$=9.4 k$\Omega$, $R_2$=5 k$\Omega$, and $R_2$=1 k$\Omega$.

SPICE Simulation tests have been done using second-order low pass filter (LPF) with frequency scaling technique and values of C=100 pF, $R_1$=10 KΩ for different cases of $R_2$. Using Monte Carlo analysis, the filter has been extensively simulated for 100 runs with an applied resistance tolerance of 1% to $R_1$ and $R_2$ to check the reliability of the proposed filter. The frequency responses of three different cases, namely $R_2$=9.41 kΩ, $R_2$=5 kΩ and $R_2$=1 kΩ, are provided in plot 400 of FIG. 4. The pole frequency is scaled down from 1.43 MHz to approximately 9.9 kHz for $R_2$=9.4 kΩ by controlling only $R_2$.

Figure 5:
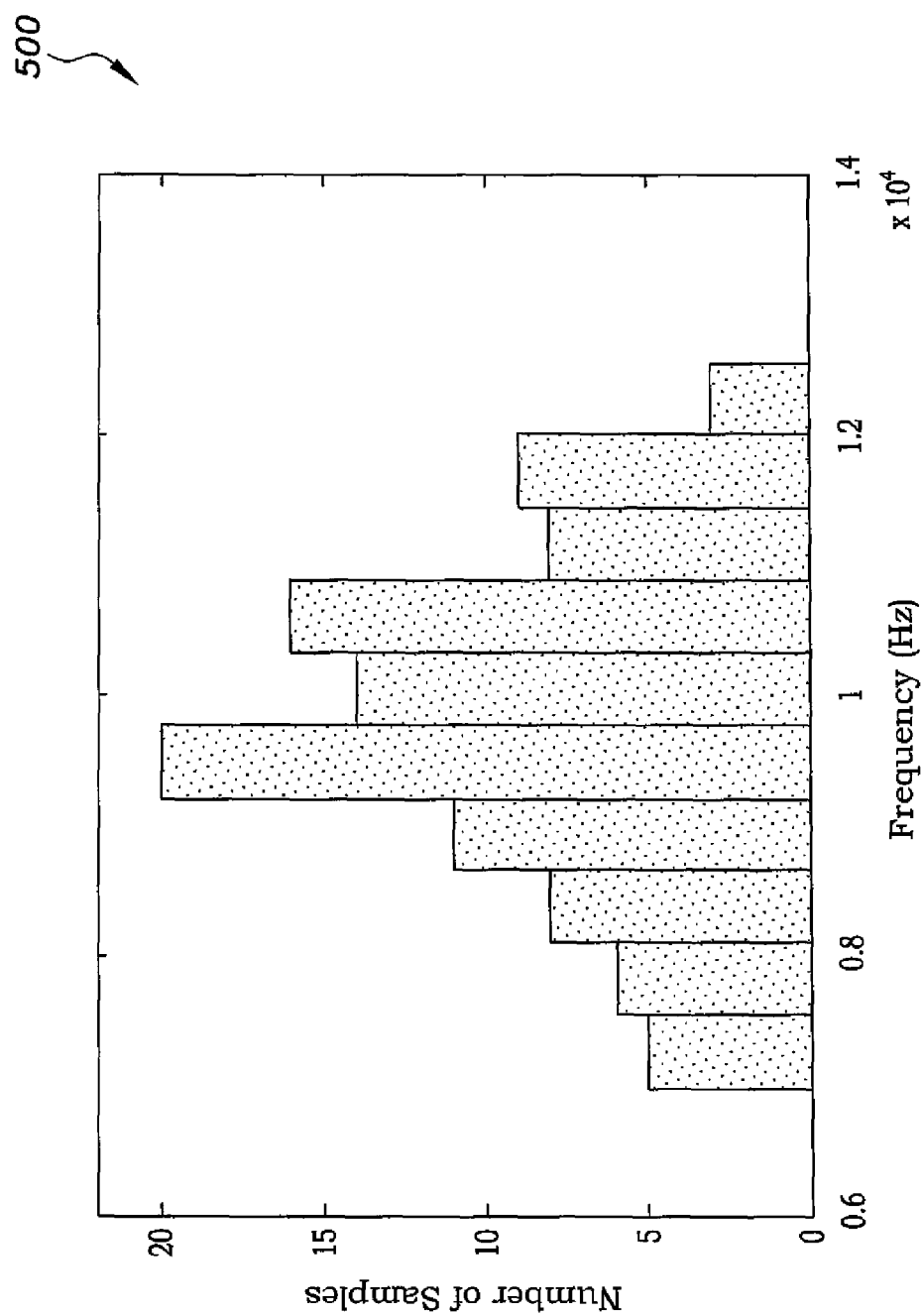
FIG. 5 is a sample histogram plot of the low frequency filter for biomedical applications according to the present invention when $R_2$=9.4 k$\Omega$.

The histogram 500 of FIG. 5 shows one case where a 4-bit pole frequency reduction is achieved when $R_2$=9.4 kΩ, which represents the distribution of the samples developed by Monte Carlo analysis over a range of frequencies. Table 1 summarizes the results obtained from the conducted simulation and percentage of error.

The inference drawn from Table 1 is that this technique can be used for both directions, upscaling and downscaling. Capacitor arrays can be incorporated to introduce a 30% tuning in the pole frequency. As a result, a 5-bit pole frequency reduction can be realized, as indicated in Table 1, giving a probability of p=0.76 and a 6-bit reduction if we allow 50% tuning. This technique can be combined with other techniques, an R2R approach, for example, to realize a very low pole frequency on the order of 0.1 Hz.

TABLE 1

Summary of the Monte Carlo simulation

| $R_2$ (kΩ) | Number of Bit Reduction, n | Pole Frequency (kHz) | Deviation from Nominal value | In Range Samples out of 100 |
|---|---|---|---|---|
| 1 | NA | 1432.4 | 1.33% | 100 |
| 5 | NA | 159.155 | 3% | 100 |
| 8.9 | 3 bits | 19892 | 10% | 82 |
| 9.4 | 4 bits | 9943 | 20% | 81 |
| 9.7 | 5 bits | 4973 | 30% | 76 |
| 9.85 | 6 bits | 2489 | 50% | 63 |

It is to be understood that the present invention is not limited to the embodiments described above, but encompasses any and all embodiments within the scope of the following claims.

We claim:
1. A low frequency filter, comprising:
a non-integrating operational amplifier circuit having an input and an output;
a two-integrator loop filter circuit having a first operational amplifier integrator and a second operational amplifier (Op-Amp) integrator fed by the first operational amplifier integrator, the non-integrating operational amplifier circuit feeding the first integrator, the second Op-Amp integrator having an output feeding the input of the non-integrating operational amplifier in a loop path, thereby forming a second-order low pass filter; the first and second integrators each having an inverting input and a non-inverting input; and
a first pair of resistors $R_1$ and $R_2$ and a second pair of resistors $R_3$ and $R_4$, $R_1$ and $R_2$ having a common terminal connected to the non-inverting input of the first Op-Amp integrator and $R_3$ and $R_4$ having a common terminal connected to the non-inverting input of the second Op-Amp integrator, $R_1$ being connected to the output of the non-integrating operational amplifier, $R_3$ being connected to the output of the first operational amplifier integrator, and $R_4$ being connected in a feedback path to the input of the non-integrating operational amplifier.
2. The low frequency filter according to claim 1, wherein said two-integrator loop filter circuit has:
a first integration capacitor (C1) connected between the output and the non-inverting input of the first op-amp integrator has a value of;
a second integration capacitor (C2) connected between the output and the non-inverting input of the second op-amp integrator;
a feedback gain resistor ($R_G$) disposed between $R_4$ and the input of said non-integrating operational amplifier;
a loop feedback resistor ($R_5$) disposed in said loop path between the output of the second integrator and said non-integrating operational amplifier;
an input resistor ($R_{in}$) connected to said non-integrating operational amplifier;
a forward gain resistor ($R_f$) connected to said non-integrating operational amplifier; and
wherein said low frequency filter has a transfer function characterized by the relation,

$$\frac{V_{LP}}{V_{in}} = \frac{\frac{R_f(R_1 - R_2)(R_3 - R_4)}{C_1 C_2 R_1 R_2 R_3 R_4 R_{in}}}{S^2 + S\left(\frac{R_f(R_1 - R_2)}{C_2 R_1 R_2 R_G}\right) + \frac{R_f(R_1 - R_2)(R_3 - R_4)'}{C_1 C_2 R_1 R_2 R_3 R_4 R_5}}$$

where $V_{LP}$ represents the output of the second Op-Amp integrator and $V_{in}$ represents the input of said non-integrating operational amplifier circuit.

* * * * *